(12) United States Patent
Friedman et al.

(10) Patent No.: US 7,888,048 B2
(45) Date of Patent: Feb. 15, 2011

(54) P4HAS AS MODIFIERS OF THE IGFR PATHWAY AND METHODS OF USE

(75) Inventors: Lori S. Friedman, San Carlos, CA (US); Helen Francis-Lang, San Francisco, CA (US); Annette L. Parks, Newton, MA (US); Kenneth James Shaw, Brisbane, CA (US); Timothy S. Heuer, El Granada, CA (US); Lynn Margaret Bjerke, Sutton (GB)

(73) Assignee: Exelixis, Inc., South San Farncisco, CA (US)

(*) Notice: Subject to any disclaimer, the term of this patent is extended or adjusted under 35 U.S.C. 154(b) by 455 days.

(21) Appl. No.: 11/628,561

(22) PCT Filed: Jun. 20, 2005

(86) PCT No.: PCT/US2005/021655

§ 371 (c)(1),
(2), (4) Date: Sep. 17, 2008

(87) PCT Pub. No.: WO2006/009952

PCT Pub. Date: Jan. 26, 2006

(65) Prior Publication Data

US 2009/0025096 A1  Jan. 22, 2009

Related U.S. Application Data

(60) Provisional application No. 60/581,696, filed on Jun. 21, 2004.

(51) Int. Cl.
*G01N 33/53* (2006.01)
*G01N 31/00* (2006.01)

(52) U.S. Cl. ............................ 435/7.21; 435/7.1; 436/1; 436/501; 436/518; 424/9.1; 424/520; 422/1; 422/50; 422/61; 530/300; 530/350

(58) Field of Classification Search ................ None
See application file for complete search history.

(56) References Cited

FOREIGN PATENT DOCUMENTS

| WO | WO 01/68868 A | 9/2001 |
|----|---------------|--------|
| WO | WO 02/088363 A | 11/2002 |
| WO | WO 03/100008 A | 12/2003 |

OTHER PUBLICATIONS

Horelli-Kuitunen, et al., "The order and transcriptional orientation of the human COL13A1 and P4HA genes on chromosome 10 long arm determined by high-resolution FISH.", Genomics, Dec. 1, 1997, vol. 46, No. 2, pp. 299-302.
Sexton, et al., "Trascriptional profiling reveals suppressed erythropoiesis, up-regulated glycosis, and interferon-associated responses in murine malaria.", Journal of Infectious Diseases, Apr. 1, 2004, vol. 189, No. 7, pp. 1245-1256.
Roguska M A et al.: "An Increase in PROLYL-4-Hydroxylase Activity Occurs During the Retinoic-Acid-Induced Differentiation of Mouse Teratocarcinoma Stem Cell Lines F-9 and P-19," Journal of Biological Chemistry, (Microfilms), American Society of Biological Chemists, Baltimore, MD, US, vol. 260, No. 26, 1985, pp. 13893-13896.
Guoan Chen et al.: "Proteomic analysis of lung adenocarcinoma: Identification of a highly express set of proteins in tumors," Clinical Cancer Research, The American Association for Cancer Research, US, vol. 8, No. 7, 2002, pp. 2298-2305.
Nissi Ritva et al.: "Immunofluorescence localization of prolyl 4-hydroxylase isoenzymes and type I and II collagens in bone tumors: type I enzyme predominates in osteosarcomas and chondrosarcomas, whereas type II enzyme predominates in their benign counterparts," ACTA Histochemica, Elsevier, vol. 106, No. 2, May 18, 2004, pp. 111-121.

*Primary Examiner*—Lisa V Cook
(74) *Attorney, Agent, or Firm*—McDonnell Boehnen Hulbert & Berghoff LLP

(57) ABSTRACT

Human P4HA genes are identified as modulators of the IGFR pathway, and thus are therapeutic targets for disorders associated with defective IGFR function. Methods for identifying modulators of IGFR, comprising screening for agents that modulate the activity of P4HA are provided.

25 Claims, No Drawings

P4HAS AS MODIFIERS OF THE IGFR PATHWAY AND METHODS OF USE

REFERENCE TO RELATED APPLICATIONS

This application claims priority to U.S. provisional patent application 60/581,696 filed Jun. 21, 2004. The contents of the prior application are hereby incorporated in their entirety.

BACKGROUND OF THE INVENTION

Somatic mutations in the PTEN (Phosphatase and Tensin homolog deleted on chromosome 10) gene are known to cause tumors in a variety of human tissues. In addition, germline mutations in PTEN are the cause of human diseases (Cowden disease and Bannayan-Zonana syndrome) associated with increased risk of breast and thyroid cancer (Nelen M R et al. (1997) Hum Mol Genet, 8:1383-1387; Liaw D et al. (1997) Nat Genet, 1:64-67; Marsh D J et al. (1998) Hum Mol Genet, 3:507-515). PTEN is thought to act as a tumor suppressor by regulating several signaling pathways through the second messenger phosphatidylinositol 3,4,5 triphosphate (PIP3). PTEN dephosphorylates the D3 position of PIP3 and downregulates signaling events dependent on PIP3 levels (Maehama T and Dixon J E (1998) J Biol Chem, 22, 13375-8). In particular, pro-survival pathways downstream of the insulin-like growth factor (IGF) pathway are regulated by PTEN activity. Stimulation of the IGF pathway, or loss of PTEN function, elevates PIP3 levels and activates pro-survival pathways associated with tumorigenesis (Stambolic V et al. (1998) Cell, 95:29-39). Consistent with this model, elevated levels of insulin-like growth factors I and II correlate with increased risk of cancer (Yu H et al (1999) J Natl Cancer Inst 91:151-156) and poor prognosis (Takanami I et al, 1996, J Surg Oncol 61(3):205-8). In addition, increased levels or activity of positive effectors of the IGF pathway, such as Akt and PI(3) kinase, have been implicated in several types of human cancer (Nicholson K M and Anderson N G (2002) Cellular Signalling, 14:381-395).

In *Drosophila melanogaster*, as in vertebrates, the Insulin Growth Factor Receptor (IGFR) pathway includes the positive effectors PI(3) kinase, Akt, and PDK and the inhibitor, PTEN. These proteins have been implicated in multiple processes, including the regulation of cell growth and size as well as cell division and survival (Oldham S and Hafen E. (2003) Trends Cell Biol. 13:79-85; Garafolo R S. (2002) Trends Endocr. Metab. 13:156-162; Backman S A et al. (2002) Curr. Op. Neurobio. 12:1-7; Tapon N et al. (2001) Curr Op. Cell Biol. 13:731-737). Activation of the pathway in *Drosophila* can result in increases in cell size, cell number and organ size (Oldham S et al. (2002) Dev. 129:4103-4109; Prober D A and Edgar B A. (2002) Genes & Dev. 16:2286-2299; Potter C J et al. (2001) Cell 105:357-368; Verdu J et al. (1999) Cell Biol. 1:500-506).

Collagen prolyl 4-hydroxylases catalyze the hydroxylation of proline in x-pro-gly triplets in collagens and in proteins with collagen-like sequences. Hydroxyproline residues are essential for the folding of collagen polypeptides into triple-helical molecules. Collagen prolyl 4-hydroxylases are tetramers of 2 alpha subunits, such as P4HA3, and 2 beta subunits. P4HA3 (procollagen-proline, 2-oxoglutarate 4-dioxygenase (proline 4-hydroxylase), alpha polypeptide III) is one of several different types of alpha subunits and provides the major part of the catalytic site of the active enzyme. Alternatively spliced transcript variants have been observed, but their full-length nature has not been determined. P4HA3 expression may play a role in atherosclerotis (Van Den Diepstraten, et al (2003) Cloning of a novel prolyl 4-hydroxylase subunit expressed in the fibrous cap of human atherosclerotic plaque. Circulation 108: 508-511).

The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as IGFR, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the IGFR pathway in *Drosophila*, and identified their human orthologs, hereinafter referred to as proline 4-hydroxylase (P4HA). The invention provides methods for utilizing these IGFR modifier genes and polypeptides to identify P4HA-modulating agents that are candidate therapeutic agents that can be used in the treatment of disorders associated with defective or impaired IGFR function and/or P4HA function. Preferred P4HA-modulating agents specifically bind to P4HA polypeptides and restore IGFR function. Other preferred P4HA-modulating agents are nucleic acid modulators such as antisense oligomers and RNAi that repress P4HA gene expression or product activity by, for example, binding to and inhibiting the respective nucleic acid (i.e. DNA or mRNA).

P4HA modulating agents may be evaluated by any convenient in vitro or in vivo assay for molecular interaction with a P4HA polypeptide or nucleic acid. In one embodiment, candidate P4HA modulating agents are tested with an assay system comprising a P4HA polypeptide or nucleic acid. Agents that produce a change in the activity of the assay system relative to controls are identified as candidate IGFR modulating agents. The assay system may be cell-based or cell-free. P4HA-modulating agents include P4HA related proteins (e.g. dominant negative mutants, and biotherapeutics); P4HA-specific antibodies; P4HA-specific antisense oligomers and other nucleic acid modulators; and chemical agents that specifically bind to or interact with P4HA or compete with P4HA binding partner (e.g. by binding to a P4HA binding partner). In one specific embodiment, a small molecule modulator is identified using a hydroxylase assay. In specific embodiments, the screening assay system is selected from a binding assay, an apoptosis assay, a cell proliferation assay, an angiogenesis assay, and a hypoxic induction assay.

In another embodiment, candidate IGFR pathway modulating agents are further tested using a second assay system that detects changes in the IGFR pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the IGFR pathway, such as an angiogenic, apoptotic, or cell proliferation disorder (e.g. cancer).

The invention further provides methods for modulating the P4HA function and/or the IGFR pathway in a mammalian cell by contacting the mammalian cell with an agent that specifically binds a P4HA polypeptide or nucleic acid. The agent may be a small molecule modulator, a nucleic acid modulator, or an antibody and may be administered to a mammalian animal predetermined to have a pathology associated with the IGFR pathway.

DETAILED DESCRIPTION OF THE INVENTION

A dominant loss of function screen was carried out in *Drosophila* to identify genes that interact with or modulate the IGFR signaling pathway. Modifiers of the IGFR pathway and their orthologs were identified. The SD05564P gene was identified as a modifier of the IGFR pathway. Accordingly, vertebrate orthologs of this modifier, and preferably the human orthologs, P4HA genes (i.e., nucleic acids and polypeptides) are attractive drug targets for the treatment of pathologies associated with a defective IGFR signaling pathway, such as cancer.

In vitro and in vivo methods of assessing P4HA function are provided herein. Modulation of the P4HA or their respective binding partners is useful for understanding the association of the IGFR pathway and its members in normal and disease conditions and for developing diagnostics and therapeutic modalities for IGFR related pathologies. P4HA-modulating agents that act by inhibiting or enhancing P4HA expression, directly or indirectly, for example, by affecting a P4HA function such as enzymatic (e.g., catalytic) or binding activity, can be identified using methods provided herein. P4HA modulating agents are useful in diagnosis, therapy and pharmaceutical development.

Nucleic Acids and Polypeptides of the Invention

Sequences related to P4HA nucleic acids and polypeptides that can be used in the invention are disclosed in Genbank (referenced by Genbank identifier (GI) number) as GI#s 54792078 (SEQ ID NO: 1) and 40255269 (SEQ ID NO:2) for nucleic acid, and GI#33589818 (SEQ ID NO:3) for polypeptide sequences.

The term "P4HA polypeptide" refers to a full-length P4HA protein or a functionally active fragment or derivative thereof. A "functionally active" P4HA fragment or derivative exhibits one or more functional activities associated with a full-length, wild-type P4HA protein, such as antigenic or immunogenic activity, enzymatic activity, ability to bind natural cellular substrates, etc. The functional activity of P4HA proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active P4HA polypeptide is a P4HA derivative capable of rescuing defective endogenous P4HA activity, such as in cell based or animal assays; the rescuing derivative may be from the same or a different species. For purposes herein, functionally active fragments also include those fragments that comprise one or more structural domains of a P4HA, such as a binding domain. Protein domains can be identified using the PFAM program (Bateman A., et al., Nucleic Acids Res, 1999, 27:260-2). For example, the 2OG-Fe(II) oxygenase superfamily domain (PFAM 03171) of P4HA from GI#33589818 (SEQ ID NO:3) is located at approximately amino acid residues 422 to 529. Methods for obtaining P4HA polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a P4HA. In further preferred embodiments, the fragment comprises the entire functionally active domain.

The term "P4HA nucleic acid" refers to a DNA or RNA molecule that encodes a P4HA polypeptide. Preferably, the P4HA polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human P4HA. Methods of identifying orthologs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000)10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine, and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a P4HA. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a P4HA under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of P4HA Nucleic Acids and Polypeptides P4HA nucleic acids and polypeptides are useful for identifying and testing agents that modulate P4HA function and for other applications related to the involvement of P4HA in the IGFR pathway. P4HA nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a P4HA protein for assays used to assess P4HA function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant P4HA is expressed in a cell line known to have defective IGFR function. The recombinant cells are used in cell-based screening assay systems of the invention, as described further below.

The nucleotide sequence encoding a P4HA polypeptide can be inserted into any appropriate expression vector. The necessary transcriptional and translational signals, including promoter/enhancer element, can derive from the native P4HA gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the P4HA gene product, the expression vector can comprise a promoter operably linked to a P4HA gene nucleic acid, one or more origins of replication, and, one or more selectable markers (e.g. thymidine kinase activity, resistance to antibiotics, etc.). Alternatively, recombinant expression vectors can be identified by assaying for the expression of the P4HA gene product based on the physical or functional properties of the P4HA protein in in vitro assay systems (e.g. immunoassays).

The P4HA protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the P4HA gene sequence is identified, the gene product can be isolated and purified using standard methods (e.g. ion exchange, affinity, and gel exclusion chromatography; centrifugation; differential solubility; electrophoresis). Alternatively, native P4HA proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of P4HA or other genes associated with the IGFR pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter P4HA expression may be used in in vivo assays to test for activity of a candidate IGFR modulating agent, or to further assess the role of P4HA in a IGFR pathway process such as apoptosis or cell proliferation. Preferably, the altered P4HA expression results in a detectable phenotype, such as decreased or increased levels of cell proliferation, angiogenesis, or apoptosis compared to control animals having normal P4HA expression. The genetically modified animal may additionally have altered IGFR expression (e.g. IGFR knockout). Preferred genetically modified animals are mammals such as primates, rodents (preferably mice or rats), among others. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous P4HA gene that results in a decrease of P4HA function, preferably such that P4HA expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse P4HA gene is used to construct a homologous recombination vector suitable for altering an endogenous P4HA gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the P4HA gene, e.g., by introduction of additional copies of P4HA, or by operatively inserting a regulatory sequence that provides for altered expression of an endogenous copy of the P4HA gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the IGFR pathway, as animal models of disease and disorders implicating defective IGFR function, and for in vivo testing of candidate therapeutic agents, such as those identified in screens described below. The candidate therapeutic agents are administered to a genetically modified animal having altered P4HA function and phenotypic changes are compared with appropriate control animals such as genetically modified animals that receive placebo treatment, and/or animals with unaltered P4HA expression that receive candidate therapeutic agent.

In addition to the above-described genetically modified animals having altered P4HA function, animal models having defective IGFR function (and otherwise normal P4HA function), can be used in the methods of the present invention. For example, a IGFR knockout mouse can be used to assess, in vivo, the activity of a candidate IGFR modulating agent identified in one of the in vitro assays described below. Preferably, the candidate IGFR modulating agent when administered to a model system with cells defective in IGFR function, produces a detectable phenotypic change in the model system indicating that the IGFR function is restored, i.e., the cells exhibit normal cell cycle progression.

Modulating Agents

The invention provides methods to identify agents that interact with and/or modulate the function of P4HA and/or the IGFR pathway. Modulating agents identified by the methods are also part of the invention. Such agents are useful in a variety of diagnostic and therapeutic applications associated with the IGFR pathway, as well as in further analysis of the P4HA protein and its contribution to the IGFR pathway. Accordingly, the invention also provides methods for modulating the IGFR pathway comprising the step of specifically modulating P4HA activity by administering a P4HA-interacting or -modulating agent.

As used herein, a "P4HA-modulating agent" is any agent that modulates P4HA function, for example, an agent that interacts with P4HA to inhibit or enhance P4HA activity or otherwise affect normal P4HA function. P4HA function can be affected at any level, including transcription, protein expression, protein localization, and cellular or extra-cellular activity. In a preferred embodiment, the P4HA-modulating agent specifically modulates the function of the P4HA. The phrases "specific modulating agent", "specifically modulates", etc., are used herein to refer to modulating agents that directly bind to the P4HA polypeptide or nucleic acid, and preferably inhibit, enhance, or otherwise alter, the function of the P4HA. These phrases also encompass modulating agents that alter the interaction of the P4HA with a binding partner, substrate, or cofactor (e.g. by binding to a binding partner of a P4HA, or to a protein/binding partner complex, and altering P4HA function). In a further preferred embodiment, the P4HA-modulating agent is a modulator of the IGFR pathway (e.g. it restores and/or upregulates IGFR function) and thus is also an IGFR-modulating agent.

Preferred P4HA-modulating agents include small molecule compounds; P4HA-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the P4HA protein or may be identified by screening compound libraries. Alternative appropriate modulators of this class are natural products, particularly secondary metabolites from organisms such as plants or fungi, which can also be identified by screening compound libraries for P4HA-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the IGFR pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific P4HA-interacting proteins are useful in a variety of diagnostic and therapeutic applications related to the IGFR pathway and related disorders, as well as in validation assays for other P4HA-modulating agents. In a preferred embodiment, P4HA-interacting proteins affect normal P4HA function, including transcription, protein expression, protein localization, and cellular or extra-cellular activity. In another embodiment, P4HA-interacting proteins are useful in detecting and providing information about the function of P4HA proteins, as is relevant to IGFR related disorders, such as cancer (e.g., for diagnostic means).

A P4HA-interacting protein may be endogenous, i.e. one that naturally interacts genetically or biochemically with a P4HA, such as a member of the P4HA pathway that modulates P4HA expression, localization, and/or activity. P4HA-modulators include dominant negative forms of P4HA-interacting proteins and of P4HA proteins themselves. Yeast two-hybrid and variant screens offer preferred methods for identifying endogenous P4HA-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An P4HA-interacting protein may be an exogenous protein, such as a P4HA-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). P4HA antibodies are further discussed below.

In preferred embodiments, a P4HA-interacting protein specifically binds a P4HA protein. In alternative preferred embodiments, a P4HA-modulating agent binds a P4HA substrate, binding partner, or cofactor.

Antibodies

In another embodiment, the protein modulator is a P4HA specific antibody agonist or antagonist. The antibodies have therapeutic and diagnostic utilities, and can be used in screening assays to identify P4HA modulators. The antibodies can also be used in dissecting the portions of the P4HA pathway responsible for various cellular responses and in the general processing and maturation of the P4HA.

Antibodies that specifically bind P4HA polypeptides can be generated using known methods. Preferably the antibody is specific to a mammalian ortholog of P4HA polypeptide, and more preferably, to human P4HA. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of P4HA which are particularly antigenic can be selected, for example, by routine screening of P4HA polypeptides for antigenicity or by applying a theoretical method for selecting antigenic regions of a protein (Hopp and Wood (1981), Proc. Nati. Acad. Sci. U.S.A. 78:3824-28; Hopp and Wood, (1983) Mol. Immunol. 20:483-89; Sutcliffe et al., (1983) Science 219:660-66) to the amino acid sequence of a P4HA. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of P4HA or substantially purified fragments thereof. If P4HA fragments are used, they preferably comprise at least 10, and more preferably, at least 20 contiguous amino acids of a P4HA protein. In a particular embodiment, P4HA-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of P4HA-specific antibodies is assayed by an appropriate assay such as a solid phase enzyme-linked immunosorbant assay (ELISA) using immobilized corresponding P4HA polypeptides. Other assays, such as radioimmunoassays or fluorescent assays might also be used.

Chimeric antibodies specific to P4HA polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

P4HA-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Non-aqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred P4HA-modulating agents comprise nucleic acid molecules, such as antisense oligomers or double stranded RNA (dsRNA), which generally inhibit P4HA activity. Preferred nucleic acid modulators interfere with the function of the P4HA nucleic acid such as DNA replication, transcription, translocation of the P4HA RNA to the site of protein translation, translation of protein from the P4HA RNA, splicing of the P4HA RNA to yield one or more mRNA species, or catalytic activity which may be engaged in or facilitated by the P4HA RNA.

In one embodiment, the antisense oligomer is an oligonucleotide that is sufficiently complementary to a P4HA mRNA to bind to and prevent translation, preferably by binding to the 5 untranslated region. P4HA-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred P4HA nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178; Hsieh A C et al. (2004) NAR 32(3):893-901).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a P4HA-specific nucleic acid modulator is used in an assay to further elucidate the role of the P4HA in the IGFR pathway, and/or its relationship to other members of the pathway. In another aspect of the invention, a P4HA-specific antisense oligomer is used as a therapeutic agent for treatment of IGFR-related disease states.

Assay Systems

The invention provides assay systems and screening methods for identifying specific modulators of P4HA activity. As used herein, an "assay system" encompasses all the components required for performing and analyzing results of an assay that detects and/or measures a particular event. In general, primary assays are used to identify or confirm a modulator's specific biochemical or molecular effect with respect to the P4HA nucleic acid or protein. In general, secondary assays further assess the activity of a P4HA modulating agent identified by a primary assay and may confirm that the modulating agent affects P4HA in a manner relevant to the IGFR pathway. In some cases, P4HA modulators will be directly tested in a secondary assay.

In a preferred embodiment, the screening method comprises contacting a suitable assay system comprising a P4HA polypeptide or nucleic acid with a candidate agent under conditions whereby, but for the presence of the agent, the system provides a reference activity (e.g. hydroxylase activity), which is based on the particular molecular event the screening method detects. A statistically significant difference between the agent-biased activity and the reference activity indicates that the candidate agent modulates P4HA activity, and hence the IGFR pathway. The P4HA polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second, messengers, immunogenicty and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of P4HA and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when P4HA-interacting proteins are used in screens to identify small molecule modulators, the binding specificity of the interacting protein to the P4HA protein may be assayed by various known methods such as substrate processing (e.g. ability of the candidate P4HA-specific binding agents to function as negative effectors in P4HA-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit P4HA specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a P4HA polypeptide, a fusion protein thereof, or to cells or membranes bearing the polypeptide or fusion protein. The P4HA polypeptide can be full length or a fragment thereof that retains functional P4HA activity. The P4HA polypeptide may be fused to another polypeptide, such as a peptide tag for detection or anchoring, or to another tag. The P4HA polypeptide is preferably human P4HA, or is an ortholog or derivative thereof as described above. In a preferred embodiment, the screening assay detects candidate agent-based modulation of P4HA interaction with a binding target, such as an endogenous or exogenous protein or other substrate that has P4HA-specific binding activity, and can be used to assess normal P4HA gene function.

Suitable assay formats that may be adapted to screen for P4HA modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate P4HA and IGFR pathway modulators (e.g. U.S. Pat. Nos. 5,550,019 and 6,133,437 (apoptosis assays); and U.S. Pat. Nos. 5,976,782, 6,225,118 and 6,444,434 (angio-genesis assays), among others). Specific preferred assays are described in more detail below.

High throughput assays for hydroxylase enzymes that measure comsumption of 2-oxoglutarate using fluorescence derivatization are known and have been described (c Neill et al (2005) BMG Labtech, application note 132).

Apoptosis assays. Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phospho-histone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as Cellomics™ ArrayScan® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses a P4HA, and that optionally has defective IGFR function (e.g. IGFR is over-expressed or under-expressed relative to wild-type cells). A test agent can be added to the apoptosis assay system and changes in induction of apoptosis relative to controls where no test agent is added, identify candidate IGFR modulating agents. In some embodiments of the invention, an apoptosis assay may be used as a secondary assay to test a candidate IGFR modulating agents that is initially identified using a cell-free assay system. An apoptosis assay may also be used to test whether P4HA function plays a direct role in apoptosis. For example, an apoptosis assay may be performed on cells that over- or under-express P4HA relative to wild type cells. Differences in apoptotic response compared to wild type cells suggests that the P4HA plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.#G5421).

Cell proliferation may also be assayed by colony formation in soft agar, or clonogenic survival assay (Sambrook et al., Molecular Cloning, Cold Spring Harbor (1989)). For example, cells transformed with P4HA are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a P4HA may be stained with propidium iodide and evaluated in a flow cytometer (available from Becton Dickinson), which indicates accumulation of cells in different stages of the cell cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of PI3 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).]

Accordingly, a cell proliferation or cell cycle assay system may comprise a cell that expresses a P4HA, and that optionally has defective IGFR function (e.g. IGFR is over-expressed or under-expressed relative to wild-type cells). A test agent can be added to the assay system and changes in cell proliferation or cell cycle relative to controls where no test agent is added, identify candidate IGFR modulating agents. In some embodiments of the invention, the cell proliferation or cell cycle assay may be used as a secondary assay to test a candidate IGFR modulating agents that is initially identified using another assay system such as a cell-free assay system. A cell proliferation assay may also be used to test whether P4HA function plays a direct role in cell proliferation or cell cycle. For example, a cell proliferation or cell cycle assay may be performed on cells that over- or under-express P4HA relative to wild type cells. Differences in proliferation or cell cycle compared to wild type cells suggests that the P4HA plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells trough membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a P4HA, and that optionally has defective IGFR function (e.g. IGFR is over-expressed or under-expressed relative to wild-type cells). A test agent can be added to the angiogenesis assay system and changes in angiogenesis relative to controls where no test agent is added, identify candidate IGFR modulating agents. In some embodiments of the invention, the angiogenesis assay may be used as a secondary assay to test a candidate IGFR modulating agents that is initially identified using another assay system. An angiogenesis assay may also be used to test whether P4HA function plays a direct role in cell proliferation. For example, an angiogenesis assay may be performed on cells that over- or under-express P4HA relative to wild type cells. Differences in angiogenesis compared to wild type cells suggests that the P4HA plays a direct role in angiogenesis. U.S. Pat. Nos. 5,976,782, 6,225,118 and 6,444, 434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with P4HA in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a P4HA, and that optionally has defective IGFR function (e.g. IGFR is over-expressed or under-expressed relative to wild-type cells). A test agent can be added to the hypoxic induction assay system and changes in hypoxic response relative to controls where no test agent is added, identify candidate IGFR modulating agents. In some embodiments of the invention, the hypoxic induction assay may be used as a secondary assay to test a candidate IGFR modulating agents that is initially identified using another assay system. A hypoxic induction assay may also be used to test whether P4HA function plays a direct role in the hypoxic response. For example, a hypoxic induction assay may be performed on cells that over- or under-express P4HA relative to wild type cells. Differences in hypoxic response compared to wild type cells suggests that the P4HA plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the P4HA protein. Methods for testing antibody affinity and specificity are well known in the art (Harlow and Lane, 1988, 1999, supra). The enzyme-linked immunosorbant assay (ELISA) is a preferred method for detecting P4HA-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance P4HA gene expression, preferably mRNA expression. In general, expression analysis comprises comparing P4HA expression in like populations of cells (e.g., two pools of cells that endogenously or recombinantly express P4HA) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that P4HA mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the P4HA protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve P4HA mRNA expression, may also be used to test nucleic acid modulators.

Secondary Assays

Secondary assays may be used to further assess the activity of P4HA-modulating agent identified by any of the above methods to confirm that the modulating agent affects P4HA in a manner relevant to the IGFR pathway. As used herein, P4HA-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with P4HA.

Secondary assays generally compare like populations of cells or animals (e.g., two pools of cells or animals that endogenously or recombinantly express P4HA) in the presence and absence of the candidate modulator. In general, such assays test whether treatment of cells or animals with a candidate P4HA-modulating agent results in changes in the IGFR pathway in comparison to untreated (or mock- or placebo-treated) cells or animals. Certain assays use "sensitized genetic backgrounds", which, as used herein, describe cells or animals engineered for altered expression of genes in the IGFR or interacting pathways.

Cell-Based Assays

Cell based assays may detect endogenous IGFR pathway activity or may rely on recombinant expression of IGFR pathway components. Any of the aforementioned assays may be used in this cell-based format. Candidate modulators are typically added to the cell media but may also be injected into cells or delivered by any other efficacious means.

Animal Assays

A variety of non-human animal models of normal or defective IGFR pathway may be used to test candidate P4HA modulators. Models for defective IGFR pathway typically use genetically modified animals that have been engineered to mis-express (e.g., over-express or lack expression in) genes involved in the IGFR pathway. Assays generally require systemic delivery of the candidate modulators, such as by oral administration, injection, etc.

In a preferred embodiment, IGFR pathway activity is assessed by monitoring neovascularization and angiogenesis. Animal models with defective and normal IGFR are used to test the candidate modulator's affect on P4HA in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the P4HA. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on P4HA is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the P4HA endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorigenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a preexisting tumor or a tumor cell line. After an appropriate period of time, generally around six days, the implanted samples are harvested for evaluation of the candidate modulator. Tumorigenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific P4HA-modulating agents are useful in a variety of diagnostic and therapeutic applications where disease or disease prognosis is related to defects in the IGFR pathway, such as angiogenic, apoptotic, or cell proliferation disorders. Accordingly, the invention also provides methods for modulating the IGFR pathway in a cell, preferably a cell predetermined to have defective or impaired IGFR function (e.g. due to overexpression, underexpression, or misexpression of IGFR, or due to gene mutations), comprising the step of administering an agent to the cell that specifically modulates P4HA activity. Preferably, the modulating agent produces a detectable phenotypic change in the cell indicating that the IGFR function is restored. The phrase "function is restored", and equivalents, as used herein, means that the desired phenotype is achieved, or is brought closer to normal compared to untreated cells. For example, with restored IGFR function, cell proliferation and/or progression through cell cycle may normalize, or be brought closer to normal relative to untreated cells. The invention also provides methods for treating disorders or disease associated with impaired IGFR function by administering a therapeutically effective amount of a P4HA-modulating agent that modulates the IGFR pathway. The invention further provides methods for modulating P4HA function in a cell, preferably a cell pre-determined to have defective or impaired P4HA function, by administering a P4HA-modulating agent. Additionally, the invention provides a method for treating disorders or disease associated with impaired P4HA function by administering a therapeutically effective amount of a P4HA-modulating agent.

The discovery that P4HA is implicated in IGFR pathway provides for a variety of methods that can be employed for the diagnostic and prognostic evaluation of diseases and disorders involving defects in the IGFR pathway and for the identification of subjects having a predisposition to such diseases and disorders.

Various expression analysis methods can be used to diagnose whether P4HA expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallionieimi O P, Ann Med 2001, 33:142-147; Blohm and Guiseppi-Elie, Curr Opin Biotechnol 2001, 12:41-47). Tissues having a disease or disorder implicating defective IGFR signaling that express a P4HA, are identified as amenable to treatment with a P4HA modulating agent. In a preferred application, the IGFR defective tissue overexpresses a P4HA relative to normal tissue. For example, a Northern blot analysis of mRNA from tumor and normal cell lines, or from tumor and matching normal tissue samples from the same patient, using full or partial P4HA cDNA sequences as probes, can determine whether particular tumors express or overexpress P4HA. Alternatively, the TaqMan® is used for quantitative RT-PCR analysis of P4HA expression in cell lines, normal tissues and tumor samples (PE Applied Biosystems).

Various other diagnostic methods may be performed, for example, utilizing reagents such as the P4HA oligonucleotides, and antibodies directed against a P4HA, as described above for: (1) the detection of the presence of P4HA gene mutations, or the detection of either over- or under-expression of P4HA mRNA relative to the non-disorder state; (2) the detection of either an over- or an under-abundance of P4HA gene product relative to the non-disorder state; and (3) the detection of perturbations or abnormalities in the signal transduction pathway mediated by P4HA.

Kits for detecting expression of P4HA in various samples, comprising at least one antibody specific to P4HA, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in P4HA expression, the method comprising: a) obtaining a biological sample from the patient; b) contacting the sample with a probe for P4HA expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* IGFR Screen

A dominant loss of function screen was carried out in *Drosophila* to identify genes that interact with or modulate the IGFR signaling pathway. Activation of the pathway by overexpression of IGFR at early stages in the developing *Drosophila* eye leads to an increase in cell number which results in a larger and rougher adult eye (Potter C J et al. (2001) Cell 105:357-368; Huang et al., 1999. Dev. 126:5365-5372). We generated a fly stock with an enlarged eye due to overexpression of IGFR and identified modifiers of this phenotype. We then identified human orthologues of these modifiers.

The screening stock carried two transgenes. The genotype is as follows:

+; +; P{DmIGFR-pExp-UAS)} P{Gal4-pExp-1Xey}/TM6B

Screening stock females of the above genotype were crossed to males from a collection of 3 classes of piggyBac-based transposons. The resulting progeny, which contain both the transgenes and the transposon, were scored for the effect of the transposon on the eye overgrowth phenotype (either enhancement, suppression or no effect). All data was recorded and all modifiers were retested with a repeat of the original cross. Modifiers of the eye phenotype were identified as members of the IGFR pathway. SD05564P was an enhancer a suppressor of the eye phenotype. Orthologs of the modifiers are referred to herein as P4HA.

BLAST analysis (Altschul et al., supra) was employed to identify orthologs of *Drosophila* modifiers. [For example, representative sequences from P4HA, GI#33589818 (SEQ ID NO:3), shares 38% amino acid identity with the *Drosophila* SD05564P.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 November; 10(11):1679-89) programs. For example, the 2OG-Fe(II) oxygenase superfamily domain (PFAM 03171) of P4HA from GI#33589818 (SEQ ID NO:3) is located at approximately amino acid residues 422 to 529.

II. High-Throughput In Vitro Fluorescence Polarization Assay

Fluorescently-labeled P4HA peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of P4HA activity.

III. High-Throughput In Vitro Binding Assay.

$^{33}$P-labeled P4HA peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate IGFR modulating agents.

IV. Immunoprecipitations and Immunoblotting

For coprecipitation of transfected proteins, 3×10$^6$ appropriate recombinant cells containing the P4HA proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TaqMan® analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan® assay (Applied Biosystems, Foster City, Calif.) were prepared according to the TaqMan® protocols, and the following criteria: a) primer pairs were designed to span introns to eliminate genomic contamination, and b) each primer pair produced only one product. Expression analysis was performed using a 7900HT instrument.

TaqMan® reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| Gene Name | P4HA3 |
|---|---|
| Breast | 65% |
| # of Pairs | 31 |
| Colon | 52% |
| # of Pairs | 33 |
| Head And Neck | 67% |
| # of Pairs; | 12 |
| Liver | 33% |
| # of Pairs | 9 |
| Lung | 55% |
| # of Pairs | 40 |
| Lymphoma | 0% |
| # of Pairs | 4 |
| Ovary | 32% |
| # of Pairs | 19 |
| Pancreas | 82% |
| # of Pairs | 11 |
| Prostate | 29% |
| # of Pairs | 24 |
| Skin | 29% |
| # of Pairs | 7 |
| Stomach | 67% |
| # of Pairs | 9 |
| Testis | 0% |
| # of Pairs | 8 |
| Thyroid Gland | 7% |
| # of Pairs | 14 |
| Uterus | 14% |
| # of Pairs | 21 |

VI. P4HA Functional Assays

RNAi experiments were carried out to knock down expression of P4HA (SEQ ID NO:3) in various cell lines using small interfering RNAs (siRNA, Elbashir et al, supra).

Effect of P4HA RNAi on cell proliferation and growth. BrdU and Cell Titer-Glo™ assays, as described above, were employed to study the effects of decreased P4HA expression on cell proliferation. The results of these experiments indicated that RNAi of P4HA decreased proliferation in U87MG glioblastoma cells.

Effect of P4HA RNAi on apoptosis. The Phospho-histone H2B assay, as described above, was also employed to study the effects of decreased P4HA expression on apoptosis. The results of this experiment indicated that RNAi of P4HA increased apoptosis in 231T breast cancer and A549 lung cancer cells.

Multiple parameter apoptosis assay, as described above, was also used to study the effects of decreased P4HA expression on apoptosis. The results of this experiment indicated that RNAi of P4HA increased apoptosis in A2780 ovarian cancer cells, and also caused reduction of cell count in these same cells.

Involvement in PTEN/IGF pathway: P4HA FOXO nuclear translocation assays. FOXO nuclear translocation assays, as described above, were employed to assess involvement of P4HA in the PTEN/IGF pathway: In these experiments, cells with reduced expression of P4HA by RNAi were transiently transfected with a plasmid expressing GFP-tagged FOXO. Automated imaging of cellular components, such as nucleus and cytoplasm were then carried out to assess translocation of FOXO. Alternatively, cells were co-transfected with siRNA directed to P4HA along with a plasmid containing FOXO, and a cassette containing a promoter, a FOXO response element, and luciferase. Cells were then analyzed for luciferase activity and compared with cells with no siRNA. Results indicated that reduced expression of P4HA led to translocation of FOXO to the cytoplasm, similar to loss of PTEN. These results suggest involvement of P4HA in the PTEN/IGFR pathway.

Pan-AKT assays. This assay was developed to detect involvement of P4HA in the PTEN/IGFR pathway. The assay detects changes in phosphorylation for several substrates of AKT, such as PRAS40, BAD, 4EBP1, and RPS6. For this experiment, antibodies were raised against phosphorylated AKT substrates, including the consensus phosphorylated AKT substrate sequence RxRxxS/T. Expression levels of phosphorylated substrates were then quantitated at normal levels, in presence of a negative control, a positive control (AKT), and then with P4HA knockout.

We used BAD as the substrate for a subset of the experiments. For this substrate, AKT pathway inhibition causes decreased cytoplasmic staining and unchanged or increased nuclear staining. Cells were plated in 96 well plates, transfected with RNAi for P4HA, fixed, permeabilized and stained with anti-phospho-BAD antibody. Measurements were based on the percentage of the population of cells with a decreased Cytoplasmic/Nuclear staining ratio compared with negative or positive control cells. Results of this experiment showed that reduced expression of P4HA caused a reduction in the level of phospho-BAD protein in the cytoplasm in 231T breast cancer and PC3 prostate cancer cells, thus suggesting an involvement in the IGFR pathway.

We used PRAS40 as the substrate for another subset of experiments. For this substrate, pathway inhibition causes decreased cytoplasmic staining and increased nuclear and perinuclear staining. Cells were plated in 96 well plates, transfected with RNAi for P4HA, fixed, treated with PRAS40 antibody, and stained. Measurements were based on percentage of population of cells with increased or decreased nuclear/cytoplasmic staining ratio compared with negative or positive control cells. Results of this experiment showed that reduced expression of P4HA caused an alteration in the level of phospho PRAS40 protein in PC3 cells, thus suggesting an involvement in the IGFR pathway. Taken together, the results of the pan-AKT assay suggest involvement of P4HA in the PTEN/IGF pathway.

What is claimed is:

1. A method of identifying a candidate IGFR pathway modulating agent, said method comprising the steps of:
   (a) providing an assay system comprising a P4HA polypeptide or nucleic acid;
   (b) contacting the assay system with a test agent under conditions whereby, but for the presence of the test agent, the system provides a reference activity; and
   (c) detecting a test agent-biased activity of the assay system, wherein a difference between the test agent-biased activity and the reference activity identifies the test agent as a candidate IGFR pathway modulating agent.

2. The method of claim 1 wherein the assay system comprises cultured cells that express the P4HA polypeptide.

3. The method of claim 2 wherein the cultured cells additionally have defective IGFR function.

4. The method of claim 1 wherein the assay system includes a screening assay comprising a P4HA polypeptide, and the candidate test agent is a small molecule modulator.

5. The method of claim 4 wherein the assay is a hydroxylase assay.

6. The method of claim 1 wherein the assay system is selected from the group consisting of an apoptosis assay system, a cell proliferation assay system, an angiogenesis assay system, and a hypoxic induction assay system.

7. The method of claim 1 wherein the assay system includes a binding assay comprising a P4HA polypeptide and the candidate test agent is an antibody.

8. The method of claim 1 wherein the assay system includes an expression assay comprising a P4HA nucleic acid and the candidate test agent is a nucleic acid modulator.

9. The method of claim 8 wherein the nucleic acid modulator is an antisense oligomer.

10. The method of claim 8 wherein the nucleic acid modulator is a PMO.

11. The method of claim 1 additionally comprising:
    (d) administering the candidate IGFR pathway modulating agent identified in (c) to a model system comprising cells defective in IGFR function and, detecting a phenotypic change in the model system that indicates that the IGFR function is restored.

12. The method of claim 11 wherein the model system is a mouse model with defective IGFR function.

13. A method for modulating a IGFR pathway of a cell comprising contacting a cell defective in IGFR function with a candidate modulator that specifically binds to a P4HA polypeptide, whereby IGFR function is restored.

14. The method of claim 13 wherein the candidate modulator is administered to a vertebrate animal predetermined to have a disease or disorder resulting from a defect in IGFR function.

15. The method of claim 13 wherein the candidate modulator is selected from the group consisting of an antibody and a small molecule.

16. The method of claim 1, comprising the additional steps of:
    (d) providing a secondary assay system comprising cultured cells or a non-human animal expressing P4HA,
    (e) contacting the secondary assay system with the test agent of (b) or an agent derived therefrom under conditions whereby, but for the presence of the test agent or agent derived therefrom, the system provides a reference activity; and
    (f) detecting an agent-biased activity of the second assay system,
    wherein a difference between the agent-biased activity and the reference activity of the second assay system confirms the test agent or agent derived therefrom as a candidate IGFR pathway modulating agent,
    and wherein the second assay detects an agent-biased change in the IGFR pathway.

17. The method of claim 16 wherein the secondary assay system comprises cultured cells.

18. The method of claim 16 wherein the secondary assay system comprises a non-human animal.

19. The method of claim 18 wherein the non-human animal mis-expresses an IGFR pathway gene.

20. A method of modulating IGFR pathway in a mammalian cell comprising contacting the cell with an agent that specifically binds a P4HA polypeptide or nucleic acid.

21. The method of claim 20 wherein the agent is administered to a mammalian animal predetermined to have a pathology associated with the IGFR pathway.

22. The method of claim 20 wherein the agent is a small molecule modulator, a nucleic acid modulator, or an antibody.

23. A method for diagnosing a disease in a patient comprising:
    obtaining a biological sample from the patient;
    contacting the sample with a probe for P4HA expression;
    comparing results from step (b) with a control;
    determining whether step (c) indicates a likelihood of disease.

24. The method of claim 23 wherein said disease is cancer.

25. The method according to claim 24, wherein said cancer is a cancer as shown in Table 1 as having >25% expression level.

* * * * *

```
                        SEQUENCE LISTING

<160> NUMBER OF SEQ ID NOS: 3

<210> SEQ ID NO 1
<211> LENGTH: 2272
<212> TYPE: DNA
<213> ORGANISM: Homo sapiens

<400> SEQUENCE: 1
gcgcggccag gactgtctga ggggaagttc gcgagcgctg gctatgggtc ctggggcgcg      60
gctggcggcg ctgctggcgg tgctggcgct cgggacagga gacccagaaa gggctgcggc     120
tcggggcgac acgttctcgg cgctgaccag cgtggcgcgc gccctggcgc ccgagcgccg     180
gctgctgggg ctgctgaggc ggtacctgcg cggggaggag gcgcggctgc gggacctgac     240
tagattctac gacaaggtac tttctttgca tgaggattca acaacccctg tggctaaccc     300
tctgcttgca tttactctca tcaaacgcct gcagtctgac tggaggaatg tggtacatag     360
tctggaggcc agtgagaaca tccgagctct gaaggatggc tatgagaagg tggagcaaga     420
ccttccagcc tttgaggacc ttgagggagc agcaagggcc ctgatgcggc tgcaggacgt     480
gtacatgctc aatgtgaaag gcctggcccg aggtgtcttt cagagagtca ctggctctgc     540
catcactgac ctgtacagcc ccaaacggct cttttctctc acaggggatg actgcttcca     600
agttggcaag gtggcctatg acatggggga ttattaccat gccattccat ggctggagga     660
ggctgtcagt ctcttccgag gatcttacgg agagtggaag acagaggatg aggcaagtct     720
agaagatgcc ttggatcact tggcctttgc ttatttccgg gcaggaaatg tttcgtgtgc     780
cctcagcctc tctcgggagt ttcttctcta cagcccagat aataagagga tggccaggaa     840
tgtcttgaaa tatgaaaggc tcttggcaga gagccccaac cacgtggtag ctgaggctgt     900
```

```
catccagagg cccaatatac cccacctgca gaccagagac acctacgagg ggctatgtca      960
gaccctgggt tcccagccca ctctctacca gatccctagc ctctactgtt cctatgagac     1020
caattccaac gcctacctgc tgctccagcc catccggaag gaggtcatcc acctggagcc     1080
ctacattgct ctctaccatg acttcgtcag tgactcagag gctcagaaaa ttagagaact     1140
tgcagaacca tggctacaga ggtcagtggt ggcatcaggg gagaagcagt tacaagtgga     1200
gtaccgcatc agcaaaagtg cctggctgaa ggacactgtt gacccaaaac tggtgaccct     1260
caaccaccgc attgctgccc tcacaggcct tgatgtccgg cctccctatg cagagtatct     1320
gcaggtggtg aactatggca tcggaggaca ctatgagcct cactttgacc atgctacgtc     1380
accaagcagc cccctctaca gaatgaagtc aggaaaccga gttgcaacat ttatgatcta     1440
tctgagctcg gtggaagctg gaggagccac agccttcatc tatgccaacc tcagcgtgcc     1500
tgtggttagg aatgcagcac tgttttggtg aacctgcac aggagtggtg aaggggacag     1560
tgacacactt catgctggct gtcctgtcct ggtgggagat aagtgggtgg ccaacaagtg     1620
gatacatgag tatggacagg aattccgcag accctgcagc tccagccctg aagactgaac     1680
tgttggcaga gagaagctgg tggagtcctg tggctttcca gagaagccag gagccaaaag     1740
ctggggtagg agaggagaaa gcagagcagc ctcctggaag aaggccttgt cagctttgtc     1800
tgtgcctcgc aaatcagagg caagggagag gttgttacca ggggacactg agaatgtaca     1860
tttgatctgc cccagccacg gaagtcagag taggatgcac agtacaaagg agggggagt     1920 ggaggcctga gagggaagtt tctggagttc agatactctc tgttgggaac aggacatctc     1980
aacagtctca ggttcgatca gtgggtcttt tggcactttg aaccttgacc acagggacca     2040
agaagtggca atgaggacac ctgcaggagg ggctagcctg actcccagaa ctttaagact     2100
ttctccccac tgccttctgc tgcagcccaa gcagggagtg tccccctccc agaagcatat     2160
cccagatgag tggtacatta tataaggatt ttttttaagt tgaaaacaac tttcttttct     2220
ttttgtatga tggttttta acacagtcat taaaaatgtt tataaatcaa aa              2272
```

<210> SEQ ID NO 2
<211> LENGTH: 2295
<212> TYPE: DNA
<213> ORGANISM: Homo sapiens
<220> FEATURE:
<221> NAME/KEY: misc_feature
<222> LOCATION: (1841)..(1841)
<223> OTHER INFORMATION: n is a, c, g, or t

<400> SEQUENCE: 2

```
gcgcggccag gactgtctga ggggaagttc gcgagcgctg gctatgggtc ctggggcgcg       60
gctggcggcg ctgctggcgg tgctggcgct cgggacagga gacccagaaa gggctgcggc      120
tcggggcgac acgttctcgg cgctgaccag cgtggcgcgc gccctggcgc ccgagcgccg      180
gctgctgggg ctgctgaggc ggtacctgcg cggggaggag gcgcggctgc gggacctgac      240
tagattctac gacaaggtac tttctttgca tgaggattca acaaccctg tggctaaccc       300 tctgcttgca tttactctca tcaaacgcct gcagtctgac tggaggaatg tggtacatag      360
tctggaggcc agtgagaaca tccgagctct gaaggatggc tatgagaagg tggagcaaga      420
ccttccagcc tttgaggacc ttgagggagc agcaagggcc ctgatgcggc tgcaggacgt      480
gtacatgctc aatgtgaaag gcctggcccg aggtgtcttt cagagagtca ctggctctgc     540
catcactgac ctgtacagcc ccaaacggct cttttctctc acaggggatg actgcttcca     600
agttggcaag gtggcctatg acatggggga ttattaccat gccattccat ggctggagga     660
```

```
ggctgtcagt ctcttccgag gatcttacgg agagtggaag acagaggatg aggcaagtct    720
agaagatgcc ttggatcact tggcctttgc ttatttccgg gcaggaaatg tttcgtgtgc    780
cctcagcctc tctcgggagt ttcttctcta cagcccagat aataaggaga tggccaggaa    840
tgtcttgaaa tatgaaaggc tcttggcaga gagccccaac cacgtggtag ctgaggctgt    900
catccagagg cccaatatac cccacctgca gaccagagac acctacgagg gctatgtca    960 gaccctgggt tcccagccca ctctctacca gatccctagc ctctactgtt cctatgagac   1020
caattccaac gcctacctgc tgctccagcc catccggaag gaggtcatcc acctggagcc   1080
ctacattgct ctctaccatg acttcgtcag tgactcagag gctcagaaaa ttagagaact   1140
tgcagaacca tggctacaga ggtcagtggt ggcatcaggg gagaagcagt acaagtgga   1200 gtaccgcatc agcaaaagtg cctggctgaa ggacactgtt gacccaaaac tggtgaccct   1260
caaccaccgc attgctgccc tcacaggcct tgatgtccgg cctccctatg cagagtatct   1320
gcaggtggtg aactatggca tcggaggaca ctatgagcct cactttgacc atgctacgtc   1380
accaagcagc cccctctaca gaatgaagtc aggaaaccga gttgcaacat ttatgatcta   1440
tctgagctcg gtggaagctg gaggagccac agccttcatc tatgccaacc tcagcgtgcc   1500
tgtggttagg aatgcagcac tgttttggtg gaacctgcac aggagtggtg aaggggacag   1560
tgacacactt catgctggct gtcctgtcct ggtgggagat aagtgggtgg ccaacaagtg   1620
gatacatgag tatggacagg aattccgcag accctgcagc tccagccctg aagactgaac   1680
tgttggcaga gagaagctgg tggagtcctg tggctttcca gagaagccag gagccaaaag   1740
ctggggtagg agaggagaaa gcatagcagc ctcctggaag aaggccttgt cagctttgtc   1800
tgtgcctcgc aaatcagagg caaggagag gttgttacca ngggacactg agaatgtaca   1860
tttgatctgc cccagccacg gaagtcagag taggatgcac agtacaaagg agggggagt   1920 ggaggcctga gagggaagtt tctggagttc agatactctc tgttgggaac aggacatctc   1980
aacagtctca ggttcgatca gtgggtcttt tggcactttg aaccttgacc acagggacca   2040
agaagtggca atgaggacac ctgcaggagg ggctagcctg actcccagaa ctttaagact   2100
ttctccccac tgccttctgc tgcagcccaa gcagggagtg tccccctccc agaagcatat   2160
cccagatgag tggtacatta taaggatt ttttttaagt tgaaaacaac tttcttttct   2220
ttttgtatga tggtttttta acacagtcat taaaaatgtt tataaatcga aaaaaaaaa   2280 aaaaaaaaaa aaaaa                                                     2295
```

<210> SEQ ID NO 3
<211> LENGTH: 544
<212> TYPE: PRT
<213> ORGANISM: Homo sapiens

<400> SEQUENCE: 3

```
Met Gly Pro Gly Ala Arg Leu Ala Ala Leu Leu Ala Val Leu Ala Leu
1               5                   10                  15

Gly Thr Gly Asp Pro Glu Arg Ala Ala Ala Arg Gly Asp Thr Phe Ser
            20                  25                  30

Ala Leu Thr Ser Val Ala Arg Ala Leu Ala Pro Glu Arg Arg Leu Leu
        35                  40                  45

Gly Leu Leu Arg Arg Tyr Leu Arg Gly Glu Glu Ala Arg Leu Arg Asp
    50                  55                  60

Leu Thr Arg Phe Tyr Asp Lys Val Leu Ser Leu His Glu Asp Ser Thr
65                  70                  75                  80
```

-continued

```
Thr Pro Val Ala Asn Pro Leu Leu Ala Phe Thr Leu Ile Lys Arg Leu
             85                  90                  95
Gln Ser Asp Trp Arg Asn Val Val His Ser Leu Glu Ala Ser Glu Asn
                100                 105                 110
Ile Arg Ala Leu Lys Asp Gly Tyr Glu Lys Val Glu Gln Asp Leu Pro
            115                 120                 125
Ala Phe Glu Asp Leu Glu Gly Ala Ala Arg Ala Leu Met Arg Leu Gln
        130                 135                 140
Asp Val Tyr Met Leu Asn Val Lys Gly Leu Ala Arg Gly Val Phe Gln
145                 150                 155                 160
Arg Val Thr Gly Ser Ala Ile Thr Asp Leu Tyr Ser Pro Lys Arg Leu
                165                 170                 175
Phe Ser Leu Thr Gly Asp Asp Cys Phe Gln Val Gly Lys Val Ala Tyr
            180                 185                 190
Asp Met Gly Asp Tyr Tyr His Ala Ile Pro Trp Leu Glu Glu Ala Val
        195                 200                 205
Ser Leu Phe Arg Gly Ser Tyr Gly Glu Trp Lys Thr Glu Asp Glu Ala
210                 215                 220
Ser Leu Glu Asp Ala Leu Asp His Leu Ala Phe Ala Tyr Phe Arg Ala
225                 230                 235                 240
Gly Asn Val Ser Cys Ala Leu Ser Leu Ser Arg Glu Phe Leu Leu Tyr
                245                 250                 255
Ser Pro Asp Asn Lys Arg Met Ala Arg Asn Val Leu Lys Tyr Glu Arg
            260                 265                 270
Leu Leu Ala Glu Ser Pro Asn His Val Val Ala Glu Ala Val Ile Gln
        275                 280                 285
Arg Pro Asn Ile Pro His Leu Gln Thr Arg Asp Thr Tyr Glu Gly Leu
290                 295                 300
Cys Gln Thr Leu Gly Ser Gln Pro Thr Leu Tyr Gln Ile Pro Ser Leu
305                 310                 315                 320
Tyr Cys Ser Tyr Glu Thr Asn Ser Asn Ala Tyr Leu Leu Leu Gln Pro
                325                 330                 335
Ile Arg Lys Glu Val Ile His Leu Glu Pro Tyr Ile Ala Leu Tyr His
            340                 345                 350
Asp Phe Val Ser Asp Ser Glu Ala Gln Lys Ile Arg Glu Leu Ala Glu
        355                 360                 365
Pro Trp Leu Gln Arg Ser Val Val Ala Ser Gly Glu Lys Gln Leu Gln
370                 375                 380
Val Glu Tyr Arg Ile Ser Lys Ser Ala Trp Leu Lys Asp Thr Val Asp
385                 390                 395                 400
Pro Lys Leu Val Thr Leu Asn His Arg Ile Ala Ala Leu Thr Gly Leu
                405                 410                 415
Asp Val Arg Pro Pro Tyr Ala Gly Tyr Leu Gln Val Val Asn Tyr Gly
            420                 425                 430
Ile Gly Gly His Tyr Glu Pro His Phe Asp His Ala Thr Ser Pro Ser
        435                 440                 445
Ser Pro Leu Tyr Arg Met Lys Ser Gly Asn Arg Val Ala Thr Phe Met
450                 455                 460
Ile Tyr Leu Ser Ser Val Glu Ala Gly Gly Ala Thr Ala Phe Ile Tyr
465                 470                 475                 480
Ala Asn Leu Ser Val Pro Val Val Arg Asn Ala Ala Leu Phe Trp Trp
                485                 490                 495
```

-continued

```
Asn Leu His Arg Ser Gly Glu Gly Asp Ser Asp Thr Leu His Ala Gly
            500                 505                 510

Cys Pro Val Leu Val Gly Asp Lys Trp Val Ala Asn Lys Trp Ile His
        515                 520                 525

Glu Tyr Gly Gln Glu Phe Arg Arg Pro Cys Ser Ser Ser Pro Glu Asp
    530                 535                 540
```